United States Patent
Takahashi et al.

(10) Patent No.: US 9,528,967 B2
(45) Date of Patent: Dec. 27, 2016

(54) LIQUID CHROMATOGRAPH AND COLUMN OVEN FOR USE THEREIN

(71) Applicant: SHIMADZU CORPORATION, Kyoto-shi, Kyoto (JP)

(72) Inventors: Kazuya Takahashi, Kyoto (JP); Yosuke Iwata, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 113 days.

(21) Appl. No.: 14/614,692

(22) Filed: Feb. 5, 2015

(65) Prior Publication Data

US 2015/0233875 A1  Aug. 20, 2015

(30) Foreign Application Priority Data

Feb. 20, 2014  (JP) ................ 2014-030710

(51) Int. Cl.
  *G01M 3/16*  (2006.01)
  *G01N 30/30*  (2006.01)
  *G01N 30/88*  (2006.01)
  *G01N 30/24*  (2006.01)

(52) U.S. Cl.
  CPC .............. *G01N 30/30* (2013.01); *G01N 30/88* (2013.01); *G01M 3/16* (2013.01); *G01N 30/24* (2013.01); *G01N 2030/3084* (2013.01); *G01N 2030/8804* (2013.01)

(58) Field of Classification Search
  CPC .......... G01M 3/16; G01M 3/04; G01M 3/007; G01M 3/40
  See application file for complete search history.

(56) References Cited

U.S. PATENT DOCUMENTS

| | | | | |
|---|---|---|---|---|
| 4,464,653 A | * | 8/1984 | Winner | G01D 18/008 324/464 |
| 6,354,143 B1 | * | 3/2002 | Isobe | F02M 25/0809 73/114.39 |
| 6,672,129 B1 | * | 1/2004 | Frederickson | A61M 15/02 347/20 |
| 6,792,794 B2 | * | 9/2004 | Bonne | G01N 1/24 73/25.01 |

(Continued)

FOREIGN PATENT DOCUMENTS

JP  2002-267644 A  9/2002

OTHER PUBLICATIONS

"TGS 813—for the detection of Combustible Gases", Figaro, Sep. 2002.*

(Continued)

*Primary Examiner* — David A Rogers
(74) *Attorney, Agent, or Firm* — Westerman, Hattori, Daniels & Adrian, LLP (57) ABSTRACT

A liquid leakage decision unit includes a leak sensor value storage part that stores a leak sensor value that is based on the intensity of a signal received from a gas sensor; a difference calculation part that, when the signal is received from the gas sensor, calculates, as a difference value, a value obtained by subtracting a previous leak sensor value stored in the leak sensor value storage part from a current leak sensor value; and a liquid leakage detection part that compares the difference value calculated by the difference calculation part with a preset threshold, thereby to detect liquid leakage in the column oven.

11 Claims, 11 Drawing Sheets

(56) References Cited

U.S. PATENT DOCUMENTS

| | | | | |
|---|---|---|---|---|
| 7,062,975 B2* | 6/2006 | Schmid | ................ | G01D 3/022 |
| | | | | 439/578 |
| 2008/0168826 A1* | 7/2008 | Saidi | ................ | G01M 3/20 |
| | | | | 73/40 |
| 2013/0318917 A1* | 12/2013 | Nilsson | ................ | G01M 3/22 |
| | | | | 53/267 |

OTHER PUBLICATIONS

"TGS813 Explosive gas detector", Figaro, http://www.figaro.co.jp/product/docs/tgs813_productionfo_rev01.pdf, (2 pages).
Office Action dated May 30, 2016, issued in counterpart Chinese Patent Application No. 201510029477.7, with English translation. (11 pages).

* cited by examiner

LIQUID CHROMATOGRAPH AND COLUMN OVEN FOR USE THEREIN

BACKGROUND OF THE INVENTION

1. Field of the Invention

The present invention relates to a liquid chromatograph including a high performance liquid chromatograph, and to a column oven for use therein.

2. Description of the Related Art

A liquid chromatograph performs separation analysis while maintaining the separation column at a constant temperature. In order to hold the column temperature constant, the separation column is placed in a column oven. The column oven includes a temperature regulator for maintaining the column oven at a constant temperature. The temperature regulator includes, for example, a block heater as a heat source, and employs an air circulation method for circulating its heat in the column.

The mobile phase of a liquid chromatograph may be a volatile solvent such as methanol, acetonitrile, or isopropyl alcohol (IPA). The separation column is connected to the analysis channel by means of a joint in the column oven, and the mobile phase may leak out through this connection portion. When the mobile phase includes a volatile solvent, vaporized gas is generated from the mobile phase leaked. If that vaporized gas is flammable, that vaporized gas has an explosive limit. Therefore, a gas sensor is provided in the oven so that the vaporized gas concentration in the column oven will not exceed the explosive limit, and monitoring is performed so that the indication by that gas sensor will not exceed a vaporization limit.

Monitoring is performed in such a way that the voltage value output from the gas sensor is read; a leak sensor value is obtained from the voltage value; and a leakage threshold is set for the leak sensor value. In order to leave some room, the leakage threshold is usually set to, for example, $\frac{1}{10}$ or $\frac{1}{20}$ of the explosive limit. If the leak sensor value exceeds the leakage threshold, an alarm is raised, or the operation of the liquid chromatograph is terminated, to prevent explosion.

Meanwhile, the concentration of an explosive limit depends on the solvent. For example, such concentration of ethanol is about 43000 ppm, while that of acetonitrile is about 30000 ppm. Thus, use of different leakage thresholds for a gas sensor according to the solvent has already been in practice (see JP 2002-267644 A: Document 1). In a method of Document 1, a plurality of solvents are each injected into a column oven until the concentration reaches a concentration that corresponds to the threshold; a value detected by the gas sensor is individually measured for each of the solvents; and each value is set as the threshold. The method of Document 1 presumes that sensitivity characteristics of the gas sensor change due to aging, and therefore solvents are injected into the oven at each time of use of each column oven, and the threshold is directly measured for each solvent in order to calibrate the sensitivity change due to aging.

It has been noticed that a system that monitors a leak sensor value based on an output of the gas sensor, and which detects leakage of a mobile phase solvent by comparing the leak sensor value with a leakage threshold as described above poses a problem in that a prolonged continuous operation of a column oven may cause a false detection of liquid leakage even when no leakage of the mobile phase solvent is present.

Figure 9:
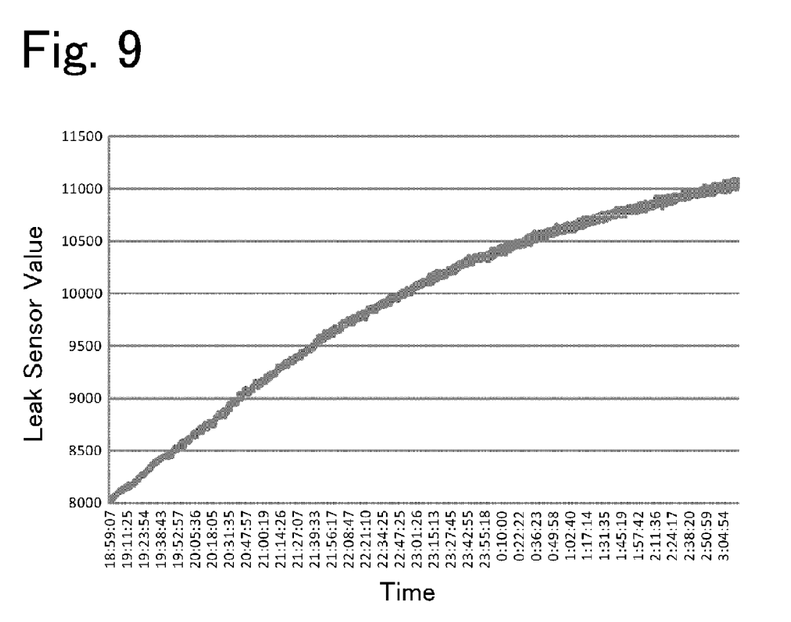
FIG. 9 is a graph illustrating one example of a temporal change of a leak sensor value.

One cause of such problem is temporal change in the sensitivity of the gas sensor. FIG. 9 illustrates an example of temporal change in a leak sensor value (described later herein) with no liquid leakage of the mobile phase solvent. The horizontal axis represents a continuous measurement from 18:59:07 to 3:04:54 next day. As can be seen from this figure, the leak sensor value, which is based on an output from the gas sensor, increases gradually over time even when no liquid leakage of the mobile phase solvent is present. Thus, if the leakage threshold is set, for example, to 10000, occurrence of liquid leakage will be detected even when no liquid leakage is present. Moreover, since the sensitivity of a gas sensor also depends on temperature and humidity, a temporal change in the temperature and/or humidity around the gas sensor may cause the leak sensor value to vary, which may also cause a false detection of liquid leakage.

SUMMARY OF THE INVENTION

Accordingly, an object of the present invention is to correctly detect liquid leakage of a mobile phase in a column oven without being affected by a temporal change in the sensitivity of the gas sensor.

A column oven according to the present invention includes a gas sensor configured to detect vaporized gas of a solvent contained in a mobile phase, which outputs a signal having an intensity dependent on a value detected, and a liquid leakage decision unit configured to receive the signal output from the gas sensor at regular time intervals to determine whether liquid leakage of the solvent is present or not, wherein the liquid leakage decision unit includes a leak sensor value storage part configured to store a leak sensor value that is based on the intensity of the signal received from the gas sensor; a difference calculation part configured to, when the signal is received from the gas sensor, identify the leak sensor value that is based on the intensity of the signal as a current leak sensor value, identify a leak sensor value that is based on an intensity of a signal previously received from the gas sensor as a previous leak sensor value, and calculate, as a difference value, a value obtained by subtracting the previous leak sensor value stored in the leak sensor value storage part from the current leak sensor value; and a liquid leakage detection part configured to compare the difference value calculated by the difference calculation part with a preset threshold, thereby to detect liquid leakage in the column oven.

That is, in the present invention, detection of liquid leakage is performed not by the absolute value of a leak sensor value based on a signal from the gas sensor, but instead by a derivative value (an amount of change per very short period of time) of a leak sensor value. The sensitivity of a gas sensor changes over time indeed, but the amount of change per very short period of time of that output signal (leak sensor value) is insignificant, and thus, a temporal change of the sensitivity of a gas sensor can be ignored over a very short period of time.

Here, although a value obtained by multiplying the output value from the gas sensor by a device-specific factor may be used as the leak sensor value, the output value from the gas sensor itself may be used instead, as the leak sensor value.

Meanwhile, since the sensitivity of a gas sensor varies depending on what solvent generates vaporized gas, the intensity of the output signal of a gas sensor varies even at a same vaporized gas concentration. Accordingly, when a leak sensor value based on the output signal of a gas sensor is used to calculate a difference between a current leak sensor value and a previous leak sensor value, such difference value also varies depending on what the solvent is, and therefore, correct detection of liquid leakage for each solvent requires a threshold to be provided for each solvent.

In this regard, the present inventors have recognized that sensitivity ratios between vaporized gases of different solvents are equivalent with respect to the same type of gas sensors. Based on this finding, a column oven in a preferred aspect of the present invention further includes a calibration factor holding part configured to retain a calibration factor (hereinafter referred to as first calibration factor) that represents a difference in sensitivity between different solvents in association with the gas sensor, and a sensor output calibration part configured to calibrate the signal received from the gas sensor by using the first calibration factor retained in the calibration factor holding part, thereby to obtain the leak sensor value. This can ensure a same level of leak sensor value between different solvents. Achieving a same level of leak sensor value used for liquid leakage detection irrespective of the solvent allows the differences between current leak sensor values and previous leak sensor values used for liquid leakage detection also to be at a same level, and thus, allows a common threshold to be used to detect liquid leakage for different solvents. The first calibration factor is provided in advance in the apparatus as an apparatus constant.

Moreover, the sensitivity of a gas sensor is subjected to aging, which, in turn, also affects a leak sensor value that is based on the output signal of a gas sensor. A reduction in sensitivity of a gas sensor over time leads to a decrease of the leak sensor value indicated for a same vaporized gas concentration, and thus, may affect liquid leakage detection. Accordingly, the calibration factor holding part retains a second calibration factor determined so that the leak sensor value remains constant if the vaporized gas concentration of a particular solvent in the column oven is a predetermined concentration. The sensor output calibration part calibrates the signal received from the gas sensor using also the second calibration factor to obtain the leak sensor value. The second calibration factor is obtained, for example, based on a value measured at a time of calibration performed on starting that column oven.

The sensitivity of a gas sensor has temperature dependence, and therefore, it is preferable that a leak sensor value be obtained also taking into account such temperature dependence. To this end, in a preferred embodiment of the present invention, the column oven further includes a temperature characteristic holding part configured to retain a temperature characteristic of the sensitivity of the gas sensor. The temperature characteristic is not measured one by one for each of the gas sensors installed, but is preset as an apparatus constant. The sensor output calibration part calibrates the signal received from the gas sensor based also on the temperature characteristic retained in the temperature characteristic holding part to obtain the leak sensor value.

The sensitivity of a gas sensor also has humidity dependence, and therefore, it is preferable that a leak sensor value be obtained also taking into account such humidity dependence. To this end, in another preferred embodiment of the present invention, the column oven further includes a humidity characteristic holding part configured to retain a humidity characteristic of the sensitivity of the gas sensor. The humidity characteristic is not measured one by one for each of the gas sensors installed, but is preset as an apparatus constant. The sensor output calibration part calibrates the signal received from the gas sensor based also on the humidity characteristic retained in the humidity characteristic holding part to obtain the leak sensor value.

The present invention is also directed to a liquid chromatograph such as a high performance liquid chromatograph. A liquid chromatograph includes a liquid feeder that feeds a mobile phase to an analysis channel having a separation column, a sample injector that injects a sample into the analysis channel between the liquid feeder and the separation column, and a detector that detects a sample component dissolved out of the separation column. In the present invention, the liquid chromatograph uses a column oven of the present invention as a column oven for adjusting the temperature of the separation column.

In the present invention, a column oven includes a liquid leakage decision unit configured to receive the output signal from the gas sensor at regular time intervals to determine whether liquid leakage of the solvent is present or not; and the liquid leakage decision unit is configured to calculate, as a difference value, a value obtained by subtracting a previous leak sensor value that is based on a signal previously received from the gas sensor from a current leak sensor value that is based on the most recent signal received from the gas sensor, and compare the difference value with a preset threshold, thereby to detect liquid leakage in the column oven. This enables effects of temporal change in the sensitivity of the gas sensor to be ignored, and thus, liquid leakage to be correctly detected. An amount of change per very short period of time of a leak sensor value when liquid leakage of a mobile phase solvent occurs is significantly greater than an amount of change per very short period of time of a leak sensor value due to a temporal change in the sensitivity of the gas sensor. Therefore, setting the threshold to a value greater than the amount of change of the leak sensor value due to a temporal change in the sensitivity of the gas sensor eliminates false detection of liquid leakage caused by a temporal change in the sensitivity of the gas sensor.

DETAILED DESCRIPTION OF THE INVENTION

Figure 1:
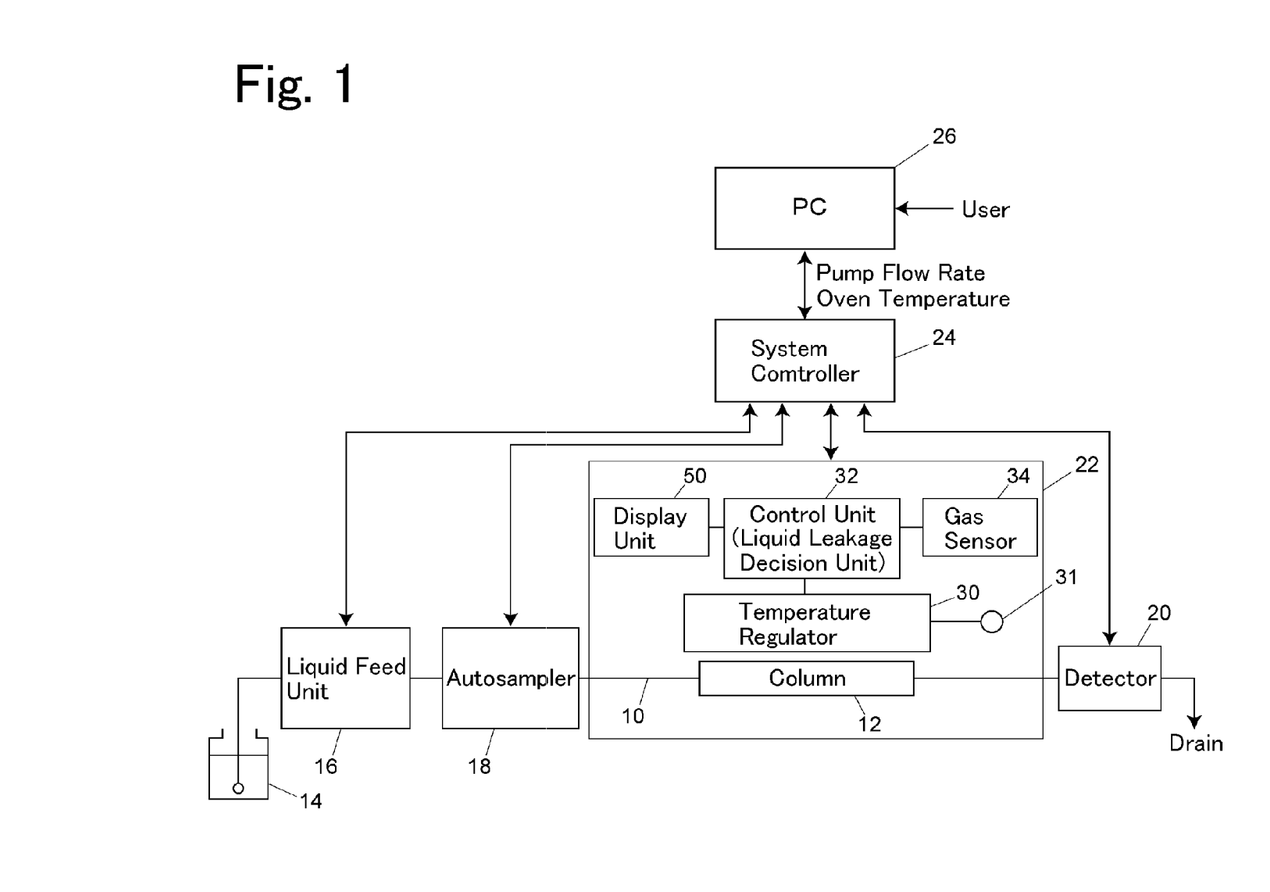
FIG. 1 is a block diagram illustrating a liquid chromatograph of one embodiment.

FIG. 1 illustrates a liquid chromatograph of one embodiment. In order to feed a mobile phase 14 to an analysis channel 10 provided with a separation column 12, a liquid feeder 16 is provided most upstream. As one example of the liquid feeder 16, a liquid feed unit is used which is configured to independently function by means of a liquid feed pump. The liquid feed unit 16 is connected to a system controller 24, and the liquid feed operation on the mobile phase is controlled according to a condition set in the system controller 24.

A sample injector 18 is provided in the analysis channel 10 between the liquid feed unit 16 and the separation column 12 in order to inject a sample into the analysis channel 10 containing the mobile phase 14 fed thereto. As one example of the sample injector 18, an autosampler 18 is used. The autosampler 18, also, is connected to the system controller 24, and injects, into the analysis channel 10, a specified amount of the sample set in the system controller 24.

A detector 20 that detects a sample component dissolved out of the separation column 12 is provided downstream of the separation column 12 in the analysis channel 10. The detector 20 includes a flow cell through which the liquid dissolved out of the separation column 12 flows, and a light detector that detects fluorescent light generated by excited light emitted to the flow cell. The light detector of the detector 20, also, is connected to the system controller 24, and a signal detected in the light detector is received by the system controller 24, where data processing is performed.

The separation column 12 is housed in a column oven 22. The column oven 22 includes a temperature regulator 30 for maintaining the separation column 12 at a constant temperature. The temperature regulator 30 is a temperature regulator of an air circulation type, including a block heater as a heat source, and a circulation mechanism that circulates air in a column oven 22. The temperature regulator includes a temperature sensor 31. Feedback control for controlling electrical continuity to the block heater so as to maintain the inside of the column oven at a constant temperature maintains the inside of the column oven 22 at a constant temperature. A control unit 32 is provided to control the temperature regulator 30.

In this embodiment, the control unit 32 also has a function as a liquid leakage decision unit that determines whether liquid leakage from the analysis channel 10 in the column oven 22 is present or not. However, the present invention is not limited thereto, and the liquid leakage decision unit may be provided separately from the control unit 32. In this embodiment, the control unit 32 is a computer such as a microprocessor provided in the column oven 22. However, the control unit 32 may be provided in the system controller 24, in which case the control unit 32 is implemented as a function of the system controller 24. In addition, the control unit 32 may be implemented by a personal computer (PC) 26, as a general-purpose computer, connected to the outside world.

The system controller 24 is connected to the personal computer 26. The personal computer 26 includes software for controlling the respective units connected to the system controller 24 (i.e., the liquid feed unit 16, the autosampler 18, the column oven 22, and the detector 20). The personal computer 26 instructs the system controller 24 on what mobile phase is to be fed by the liquid feed unit 16 and the feed amount thereof, on what sample is to be injected from the autosampler 18 and the injection amount thereof, on the oven temperature in the column oven 22, on the fluorescent light detection wavelength in the detector, etc. The system controller 24 sends necessary analysis conditions to each unit, thereby to control the operation of each unit, and receives detection signal of the detector 20 thereby to perform data processing. In addition, the system controller 24 sends, to the personal computer 26, the result of data processing based on a fluorescent light signal of the dissolved component detected by the detector 20.

A display unit 50, such as a liquid crystal display device, is provided to provide a display to inform a user of liquid leakage detection when the control unit 32 detects liquid leakage, and to provide other display. The display unit 50 may be a display unit dedicated to the column oven 22, or may be a display device of the personal computer 26.

Figure 2:
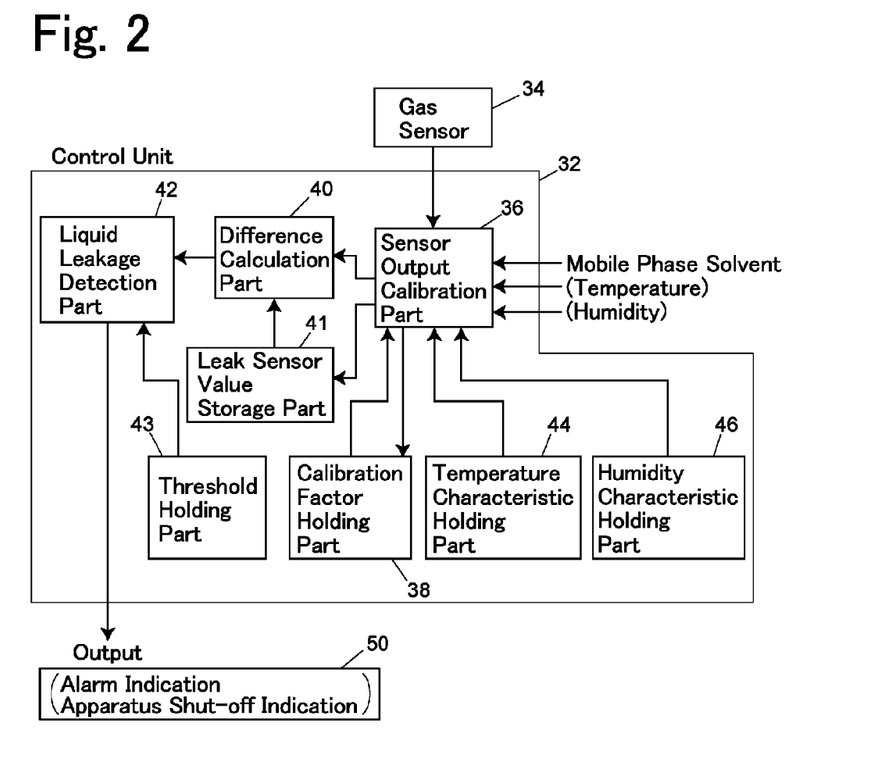
FIG. 2 is a block diagram illustrating a column oven of one embodiment.

The column oven includes therein a gas sensor 34, which, when the mobile phase leaks from the analysis channel 10, and vaporized gas is generated from a solvent contained in the mobile phase, detects the vaporized gas. As noted above, the control unit 32 not only controls the operation of the temperature regulator 30, but also includes a function as the liquid leakage decision unit that receives an output signal of the gas sensor 34, and compares the signal with a threshold, thereby to determine whether liquid leakage from the analysis channel 10 is present or not. A configuration of the control unit 32 that serves as the liquid leakage decision unit is as shown in FIG. 2.

For detection of liquid leakage, the control unit 32 includes a sensor output calibration part 36 that calibrates the output signal (voltage) from the gas sensor 34 thereby to obtain a leak sensor value; a calibration factor holding part 38 that retains a calibration factor used for that calibration; a difference calculation part 40 that, when the output signal from the gas sensor 34 is received, calculates a difference value obtained by subtracting a leak sensor value previously received from the gas sensor 34 (previous leak sensor value) from the leak sensor value that is based on the output signal (current leak sensor value); a leak sensor value storage part 41 that stores a leak sensor value; a liquid leakage detection part 42 that compares the difference value calculated by the difference calculation part 40 with a preset threshold thereby to detect liquid leakage in the column oven 22; and a threshold holding part 43 that retains a threshold used for liquid leakage detection by the liquid leakage detection part 42.

In a more preferred embodiment, the control unit 32 further includes a temperature characteristic holding part 44 that retains a temperature characteristic of the sensitivity of the gas sensor 34. In this case, the sensor output calibration part 36 is configured to calculate the leak sensor value based also on the temperature characteristic retained in the temperature characteristic holding part 44.

In a more preferred embodiment, the control unit 32 further includes a humidity characteristic holding part 46 that retains a humidity characteristic of the sensitivity of the gas sensor 34. In this case, the sensor output calibration part 36 is configured to calculate the leak sensor value based also on the humidity characteristic retained in the humidity characteristic holding part 46.

The calibration factor holding part 38, the difference calculation part 40, the threshold holding part 43, the temperature characteristic holding part 44, and the humidity characteristic holding part 46 are implemented by a storage device including a nonvolatile semiconductor memory device, such as a PROM, an EPROM, or an EEPROM, of the computer included in the control unit 32, a disk device, or other storage device. The sensor output calibration part 36 and the liquid leakage detection part 42 are implemented as functions of the computer by software installed in the computer included in the control unit 32.

The control unit 32 will now be described in more detail. The calibration factor holding part 38 retains a calibration factor (first calibration factor) for calibrating the difference in sensitivity of the gas sensor 34 depending on what the solvent is, and a calibration factor (second calibration factor) for converting the output (voltage) from the gas sensor 34 into a leak sensor value.

Sensitivity characteristics of the gas sensor are already known through literature, etc. Therefore, the first calibration factor can be obtained from known literature values, etc., or alternatively can be obtained from actual values of actual measurement performed at a predetermined solvent concentration. The first calibration factor is not obtained by measurement on each gas sensor of each column oven, but is preset as an apparatus constant.

Data for the temperature characteristic holding part 44 and for the humidity characteristic holding part 46 are also available as literature data, or alternatively can be set by using actual measurement data.

The second calibration factor is determined based on an output value of the gas sensor at the time of actual measurement at a predetermined temperature, humidity, and solvent concentration so that the leak sensor value at that time will be a predetermined value (ppm). The second calibration factor is determined, for example, during calibration before the measurement. Thus, the magnitude of the leak sensor value changes according to the second calibration factor.

The sensor output calibration part 36 obtains a leak sensor value Lk by using the first and the second calibration factors retained in the calibration factor holding part 38 according to the following equation:

$$Lk \leq V_{OUT} \times Ge_1 \times Ge_2$$

where $Ge_1$ denotes the first calibration factor; $Ge_2$ denotes the second calibration factor; and $V_{OUT}$ denotes the output value of the gas sensor.

The unit of the leak sensor value is, for example, ppm.

By calibrating the output value of the gas sensor with the first and the second calibration factors to produce a leak sensor value, the leak sensor value becomes a value that only depends on the vaporized gas concentration of the solvent. Accordingly, a same concentration yields a same leak sensor value irrespective of what the solvent is. Thus, a constant value can be used as the threshold for determining whether liquid leakage is present or not.

An output signal of the gas sensor 34 is received by the control unit 32 at regular time intervals (e.g., 0.4-second intervals). Each time an output signal of the gas sensor 34 is received by the control unit 32, the sensor output calibration part 36 obtains a leak sensor value that is based on that output value. The leak sensor value obtained by the sensor output calibration part 36 is used for calculation of a difference value in the difference calculation part 40.

The difference calculation part 40 calculates a difference $(Lk_1 - Lk_2)$ between a leak sensor value (current leak sensor value) $Lk_1$ obtained immediately after the output signal of the gas sensor 34 is received by the control unit 32 and a leak sensor value (previous leak sensor value) $Lk_2$ obtained when the output signal of the gas sensor 34 was previously received by the control unit 32, and then obtains an amount of change (derivative value) per very short period of time in the leak sensor value.

Reducing the time interval for receiving the output signal of the gas sensor 34 results in a reduction in the difference value obtained in the difference calculation part 40, while increasing that time interval results in an increase in the difference value. Although the time interval is described as 0.4 seconds herein, the time interval may be set appropriately depending on the magnitude of the output signal of the gas sensor 34.

The previous leak sensor value $Lk_2$ is stored in the leak sensor value storage part 41. The leak sensor value storage part 41 stores the leak sensor value obtained by the sensor output calibration part 36, and storage of the leak sensor value may be temporary. For example, the leak sensor value used for calculation of a difference by the difference calculation part 40 as the previous leak sensor value $Lk_2$ may be one that will be deleted.

The liquid leakage detection part 42 detects liquid leakage based on whether or not the difference value $(Lk_1 - Lk_2)$ calculated by the difference calculation part 40 exceeds the threshold retained in the threshold holding part 43. The threshold may be preset in the apparatus, or may be set based on a difference value $(Lk_1 - Lk_2)$ obtained during calibration performed before the measurement.

Figure 10:
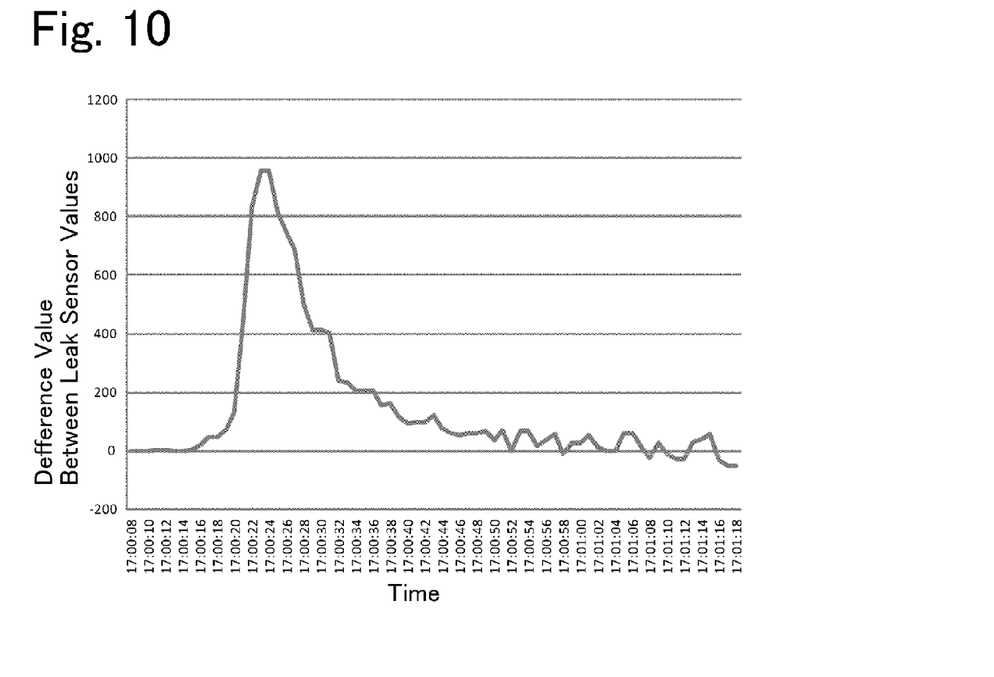
FIG. 10 is a graph illustrating one example of a temporal change of a difference value of leak sensor values when liquid leakage of a solvent is present.
Figure 11:
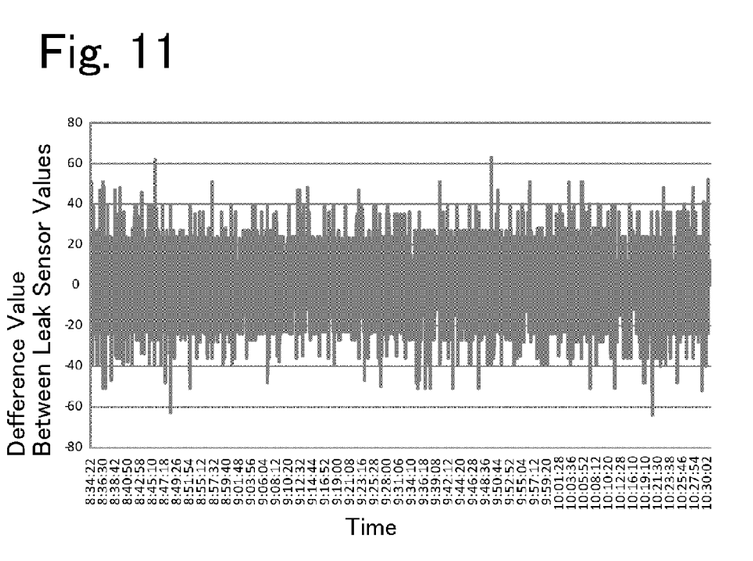
FIG. 11 is a graph illustrating one example of a temporal change of a difference value of leak sensor values when no liquid leakage of a solvent is present.

As noted above, since the sensitivity of the gas sensor changes over time, the leak sensor value based on the output of the gas sensor also changes over time even without occurrence of liquid leakage of a solvent, and the leak sensor value drifts as shown in FIG. 9. In FIG. 9 also, the leak sensor value is received at 0.4-second time intervals. However, the amount of change (difference value) per very short period of time in the leak sensor value due to such drift is low. As shown in FIG. 11, the difference value of the leak sensor value when no liquid leakage is present is at most approximately 60 to 70. In contrast, as shown in FIG. 10, the difference value of the leak sensor value sharply increases to approximately 950 when liquid leakage of a solvent occurs. Accordingly, if the threshold is set to approximately twice the maximum value of the difference value of the leak sensor value when no liquid leakage is present (e.g., 120), whether liquid leakage is present or not can be determined without being affected by a temporal change in the sensitivity of the gas sensor.

When the liquid leakage detection part 42 detects liquid leakage, for example, a display is provided to inform liquid leakage in the display unit 50; feeding the mobile phase is stopped to terminate the operation of the liquid chromatograph; or the operation of the column oven is terminated.

Figure 3:
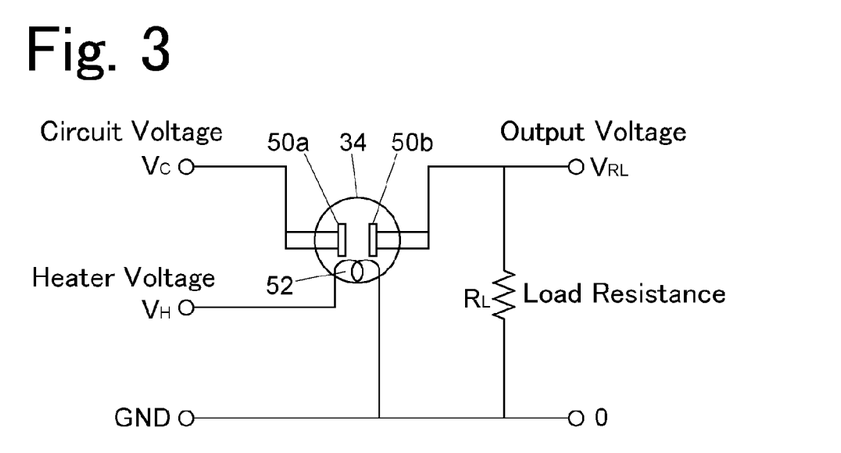
FIG. 3 is a circuit illustrating one example of a gas sensor.

One example of the gas sensor is shown in FIG. 3. No specific limitations exist on the gas sensor 34, an example of which is, however, one that uses a tin oxide ($SnO_2$) semiconductor film having low electrical conductivity as a functional film that adsorbs gas. The gas sensor 34 includes a pair of opposed electrodes 50a and 50b on the functional film that adsorbs vaporized gas of a solvent, and heater 52 that maintains the functional film at a constant temperature. Application of a constant voltage $V_H$ to the heater 52 maintains the functional film at a constant temperature. Applying a circuit voltage $V_C$ to the electrode 50a while the other electrode is grounded through a load resistor $R_L$ generates an output voltage $V_{RL}$, which is the circuit voltage $V_C$ divided by a resistance $R_S$ between the electrodes 50a and 50b, and the load resistance $R_L$:

$$V_{RL} = V_C \cdot R_L / (R_S + R_L)$$

Adsorption of vaporized gas of a solvent by the functional film between the electrodes 50a and 50b causes the resistance $R_S$ between these electrodes to decrease, and the output voltage $V_{RL}$ to rise accordingly.

Figure 4:
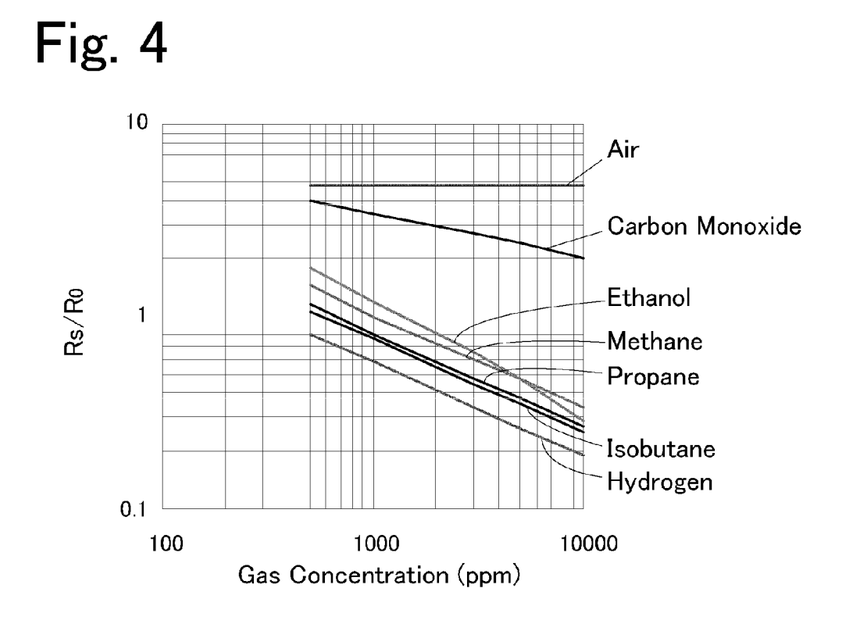
FIG. 4 is a graph illustrating a sensitivity characteristic for each solvent vaporized gas of the gas sensor.

A sensitivity characteristic representing the resistance value $R_S$ between the electrodes 50a and 50b varies depending on what the solvent gas is. FIG. 4 illustrates major sensitivity characteristics of the gas sensor (see FIGARO Product Information, Gas Sensors, Flammable Gas Sensing [online], [Search date: Oct. 27, 2014], on Internet <URL: http://www.figaro.co.jp/product/docs/tgs813_productinfo_rev01.pdf>: Document 2), and illustrates how the resistance value $R_S$ varies depending on what gas is adsorbed by the gas sensor. The horizontal axis represents the gas concentration, and the vertical axis represents the resistance values $R_S$ of methane and other gases by means of ratios thereof with respect to a resistance value $R_O$ of a reference gas, where $R_O$ denotes the resistance value of the reference gas (methane in this case) at a concentration of 1000 ppm. Note that, although acrylonitrile and other solvents often used in a liquid chromatograph are not shown here, these solvents exhibit a similar sensitivity characteristic, in which the resistance value decreases with increase in the concentration.

Figure 5:
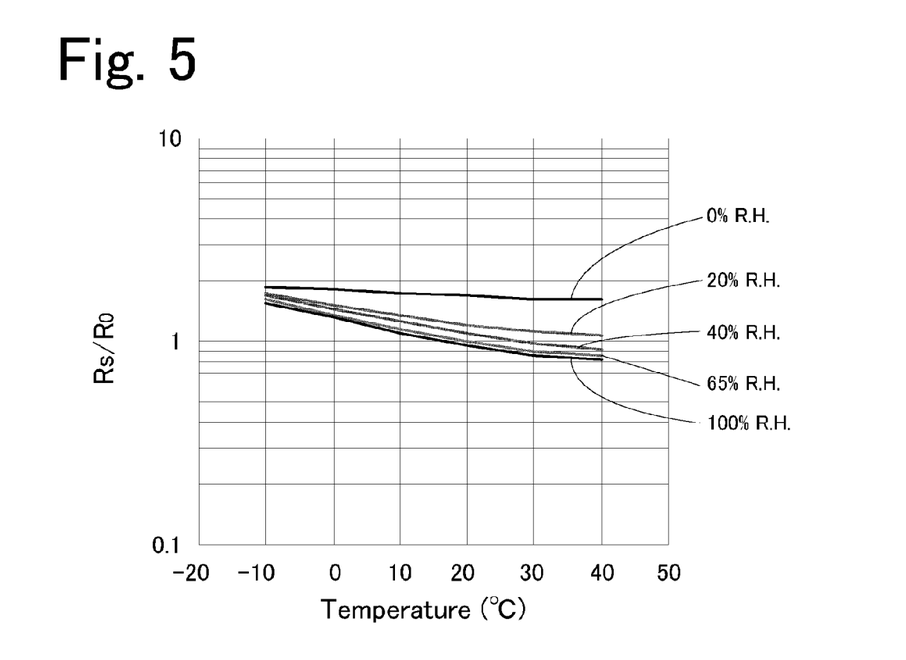
FIG. 5 is a graph illustrating temperature and humidity dependence of the gas sensor.

Sensitivity characteristics of the gas sensor exhibit dependence also on temperature and on humidity as shown in FIG. 5. FIG. 5 illustrates major sensitivity characteristics of the gas sensor that exhibit dependence on temperature and on humidity (see Document 2). The horizontal axis represents the temperature, and the vertical axis represents the resistance values $R_S$ of methane and other gases by means of ratios thereof with respect to $R_O$, where $R_O$ denotes the resistance value of the reference gas (methane in this case) at a temperature of 20° C. and a relative humidity (room humidity) of 65% RH at a concentration of 1000 ppm.

Sensitivity characteristics, temperature dependence, and humidity dependence of the gas sensor vary in the resistance value $R_S$ between individual gas sensors, but when illustrated in terms of a relative value $(R_S/R_O)$ with respect to the resistance value of vaporized gas of a particular gas as shown in FIGS. 4 and 5, no variations occur between individual gas sensors. The sensitivity characteristics, temperature dependence, and humidity dependence presented in terms of a relative value $(R_S/R_O)$ as shown in FIGS. 4 and 5 are available as literature data, or those obtained in advance by measurement on a certain gas sensor may also be applied to other gas sensors of a same type.

A first calibration factor $Ge_1$ retained in the calibration factor holding part 38 is a relative value $(R_S/R_O)$ of each solvent when the relative value $(R_S/R_O)$ of a particular solvent at a concentration corresponding to the threshold of that particular solvent (e.g., 1000 ppm) is put as 1, based on such sensitivity characteristics as those shown in FIG. 4 obtained by literature values or measurement. When the name of a solvent is input, the sensor output calibration part 36 selects and obtains a calibration factor for that solvent from the calibration factors Ge retained in the calibration factor holding part 38.

The temperature characteristic holding part 44 and the humidity specification holding unit 46 each retain data of a graph such as one shown in FIG. 5. Such data also are available as literature data, or may be obtained by measurement of a certain gas sensor. When the threshold is corrected taking into consideration the temperature and the humidity, the calibration factor holding part 38 retains the calibration factor Ge for each solvent together with the reference temperature and the reference humidity. Thus, when a temperature and a humidity are input, the sensor output calibration part 36 corrects the calibration factor based on a relative value $(R_S/R_O)$ corresponding to the input temperature and input humidity when the relative value $(R_S/R_O)$ for the reference temperature and reference humidity is put as 1. A similar process applies to cases in which only one of temperature and humidity is taken into account.

Figure 6:
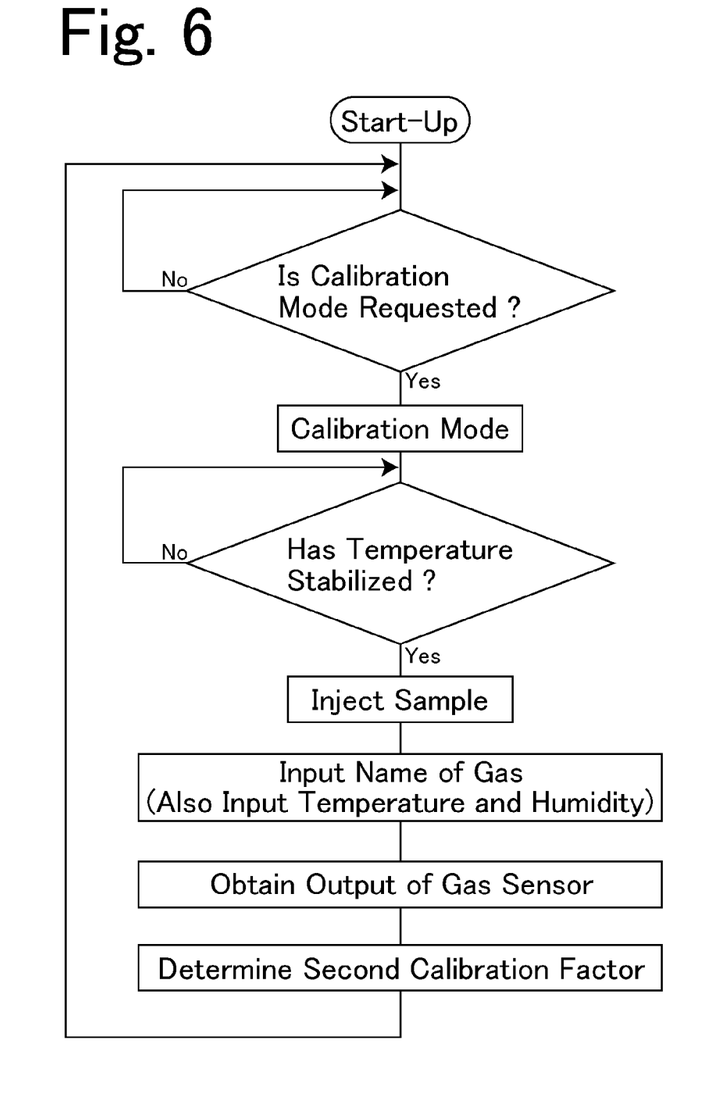
FIG. 6 is a flowchart illustrating an operation during calibration of a gas sensor according to one embodiment.

A calibration operation performed on starting the column oven will now be described referring to FIG. 6. This calibration operation determines the second calibration factor.

A user informs the apparatus of a start of calibration of the gas sensor 34 via the system controller 24, or by directly operating the column oven 22. Information input is what particular solvent is used for the calibration and the reference temperature for the calibration (hereinafter referred to as calibration reference temperature) for the column oven 22. For example, it is assumed that the user specifies methanol as the particular solvent, and 50° C. as the calibration reference temperature for the column oven 22.

When the control unit 32 receives an instruction from the system controller 24, or is instructed through a direct input to the column oven 22, the control unit 32 transitions to a calibration mode. In the calibration mode, the control unit 32 adjusts the temperature by means of the temperature regulator 30 and the temperature sensor 31 so that the temperature inside the column oven 22 will be the calibration reference temperature. When the temperature of the column oven 22 has been stabilized at the calibration reference temperature, the control unit 32 prompts the user, by means of the display unit 50, to inject a sample so that the gas concentration inside the oven will reach a calibration reference concentration.

The user injects a predetermined amount of the particular solvent so that the concentration inside the column oven 22 reaches the calibration reference concentration. A known volume of the inside of the column oven 22 allows the amount of solvent injection to be determined from the calibration reference concentration for the column oven 22.

It is confirmed that the concentration inside the column oven 22 has reached the calibration reference concentration, and the output voltage of the gas sensor at that time is obtained. Then, the second calibration factor $Ge_2$ is determined so that multiplication of this output voltage value $V_{out}$ by the second calibration factor $Ge_2$ will yield the predetermined leak sensor value, and the second calibration factor $Ge_2$ is then stored in the calibration factor holding part 38. It can be determined that the calibration reference concentration is reached by stabilization of the output of the gas sensor 34. Room humidity is input for the humidity.

Figure 7:
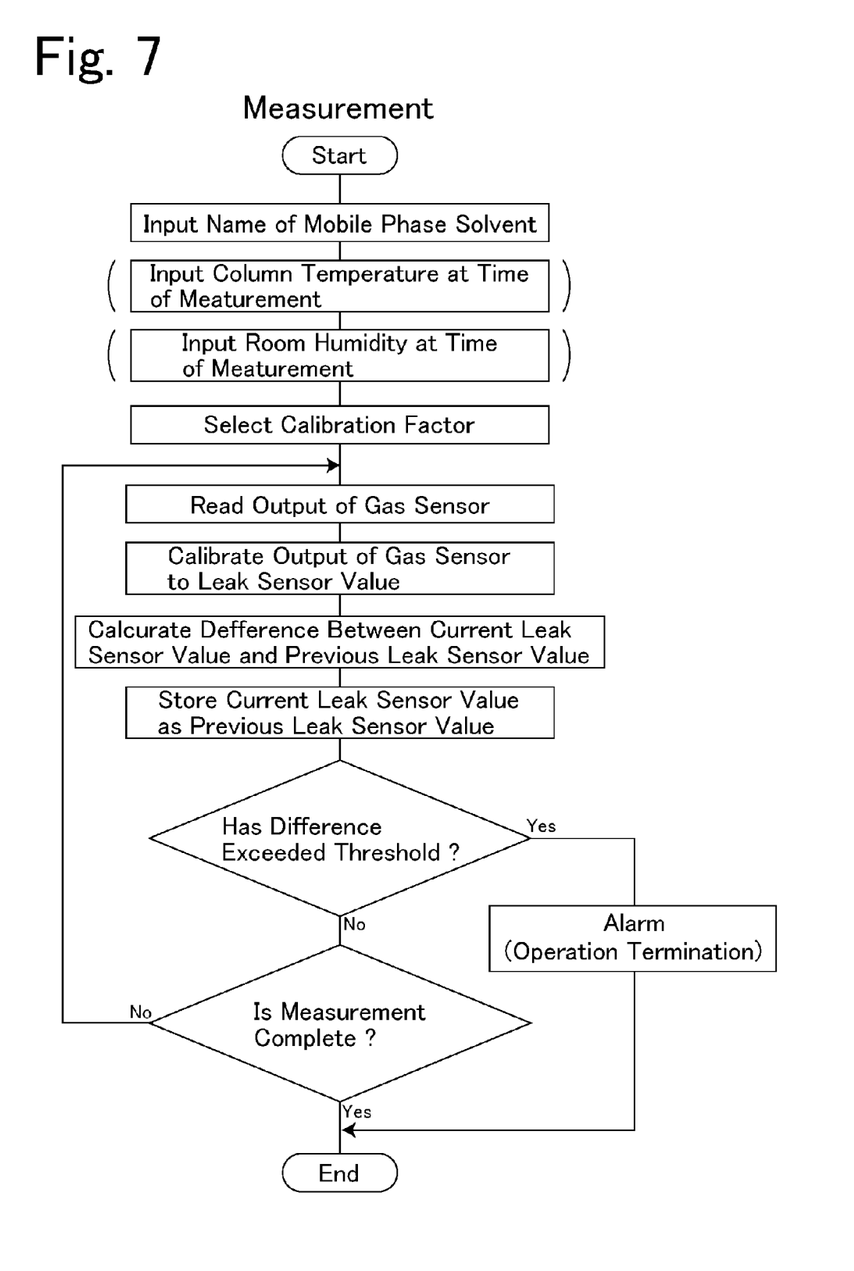
FIG. 7 is a flowchart illustrating an operation of a column oven of one embodiment.

A determination operation of liquid leakage of a solvent will now be described referring to FIG. 7.

Figure 8:
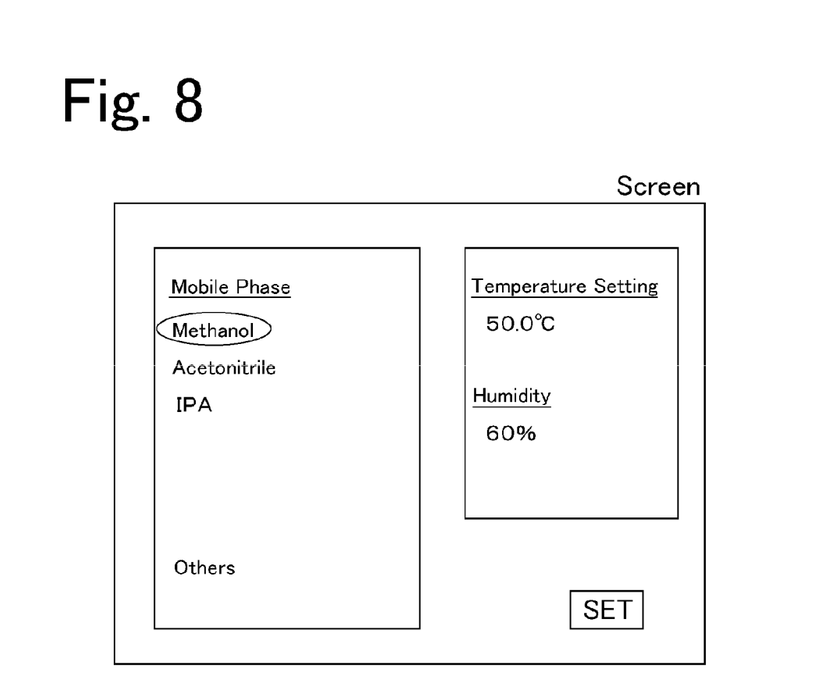
FIG. 8 is a diagram illustrating a display screen for inputting conditions to the column oven in that embodiment.

Upon starting a measurement operation, the user inputs what solvent is contained in the mobile phase used, from the system controller 24 or from the column oven 22. This information is input, for example, by using a screen of the display unit 50 as shown in FIG. 8. FIG. 8 shows a case in which methanol is input as the solvent of the mobile phase. In addition, if the threshold is corrected also using temperature and humidity, temperature and humidity settings of the column oven are also input. The temperature setting of the column oven may be set by inputting in this manner, or in such a manner that the control unit 32 automatically collects the temperature detected by the temperature sensor 31 in the column oven 22. Room humidity is input automatically or manually for the humidity.

When the solvent of the mobile phase includes only one single solvent, the name of that solvent is input. Otherwise, when the mobile phase is a mixture of two or more solvents, the name of the solvent having a lower explosive limit concentration is input. A similar process applies to cases in which the composition of the mobile phase changes over time in gradient analysis.

After the name of the solvent is input, the first calibration factor $Ge_1$ for the solvent input is selected.

Upon starting an operation of the liquid chromatograph provided with this column oven 22, the sensor output calibration part 36 obtains the leak sensor value using the first and the second calibration factors each time the control unit 32 receives an output signal from the gas sensor 34. If the leak sensor value also requires consideration of either one or both of temperature and humidity, the sensor output calibration part 36 obtains the leak sensor value based on the data retained in the temperature characteristic holding part 44 and/or the humidity characteristic holding part 46. When a leak sensor value is calculated, the difference calculation part 40 calculates a difference value obtained by subtracting the previously-obtained leak sensor value (previous leak sensor value) from this leak sensor value (current leak sensor value), and the liquid leakage detection part 42 monitors for liquid leakage by comparing the difference value with the threshold in the threshold holding part 43. The currently-obtained leak sensor value is stored in the leak sensor value storage part 41 as the previous leak sensor value, and is used for calculation for the next difference value.

If the difference value between the current leak sensor value and the previous leak sensor value exceeds the threshold during monitoring, for example, an alarm is displayed in the display unit 50, or the operation of the liquid chromatograph is terminated.

Note that, in the embodiment described above, the second calibration factor is determined based on the output value of the gas sensor at the time of actual measurement at a predetermined temperature, humidity, and solvent concentration so that a leak sensor value will be a predetermined value. This ensures that the leak sensor value obtained by the sensor output calibration part 36 is maintained at a constant level without being affected by a change in the sensitivity due to aging degradation of the gas sensor or other causes.

Meanwhile, the present invention also covers cases in which the second calibration factor is preset as an apparatus constant. However, a leak sensor value obtained based on such a second calibration factor is affected by change over time in the sensitivity of the gas sensor, and thus, the difference value between the current leak sensor value and the previous leak sensor value calculated by the difference calculation part 40 is also affected. Therefore, in such a case, the threshold is preferably calibrated based on a leak sensor value obtained during calibration. In this case, the threshold at a time when the leak sensor value is a predetermined value is retained in the threshold holding part 43 as a reference threshold; a calibration factor for the threshold is obtained based on the leak sensor value obtained during calibration; and an appropriate threshold is obtained based on this calibration factor and the reference threshold.

In addition, the present invention also covers cases in which a second calibration factor is not used. If the second calibration factor is not used, multiplying the output from the gas sensor 34 by the first calibration factor yields the leak sensor value. Also in this case, the threshold at a time when the leak sensor value is a predetermined value is retained in the threshold holding part 43 as a reference threshold; a calibration factor for the threshold is obtained based on the leak sensor value obtained during calibration; and an appropriate threshold is obtained based on this calibration factor and the reference threshold.

In the embodiment described above, effects of differences in the sensitivity of the gas sensor 34 between solvents is minimized by multiplying the output from the gas sensor 34 by the first calibration factor, but the present invention is not limited thereto. The threshold may be calibrated by the first calibration factor. In such a case, the threshold at a time when the vaporized gas concentration of a particular solvent is a predetermined value is retained in the threshold holding part 43 as a reference threshold, and this reference threshold is multiplied by the first calibration factor to obtain the threshold for liquid leakage detection.

Moreover, since the gas sensor 34 is placed inside the column oven 22, the sensitivity of the gas sensor 34 may significantly change during heating of the inside of the column oven 22. Opening and/or closure of the door of the column oven 22 may change the sensitivity of the gas sensor 34 due to possible effects of external environment. Thus, providing separate thresholds for the time of heating the column oven 22 and for the time of opening and/or closure of the door thereof, and detecting liquid leakage using these thresholds during heating of the column oven 22 and during opening and/or closure of the door thereof, can reduce the possibility of false detection of liquid leakage, and can thus improve accuracy of liquid leakage detection.

What is claimed is:

1. A column oven for adjusting a temperature of a separation column of a liquid chromatograph, the column oven comprising:
a gas sensor configured to detect vaporized gas of a solvent contained in a mobile phase, which outputs a signal having an intensity dependent on a value detected; and
a liquid leakage decision unit configured to receive the signal output from the gas sensor at regular time intervals to determine whether liquid leakage of the solvent is present or not, the liquid leakage decision unit comprising,
a leak sensor value storage part configured to store a leak sensor value that is based on the intensity of the signal received from the gas sensor,
a difference calculation part configured to, when the signal is received from the gas sensor, identify the leak sensor value that is based on the intensity of the signal as a current leak sensor value, identify a leak sensor value that is based on an intensity of a signal previously received from the gas sensor as a previous leak sensor value, and calculate, as a difference value, a value obtained by subtracting the previous leak sensor value stored in the leak sensor value storage part from the current leak sensor value, and
a liquid leakage detection part configured to detect liquid leakage in the column oven by comparing the difference value calculated by the difference calculation part with a preset threshold,
wherein the threshold is set to a value greater than an amount of change of the leak sensor value due to a temporal change in a sensitivity of the gas sensor.

2. A liquid chromatograph comprising:
a separation column;
a liquid feeder for feeding a mobile phase to an analysis channel having the separation column;
a sample injector for injecting a sample into the analysis channel between the liquid feeder and the separation column; and
a detector for detecting a sample component dissolved out of the separation column, wherein
the liquid chromatograph uses the column oven according to claim 1 as a column oven for adjusting a temperature of the separation column.

3. A column oven for adjusting a temperature of a separation column of a liquid chromatograph, the column oven comprising:
- a gas sensor configured to detect vaporized gas of a solvent contained in a mobile phase, which outputs a signal having an intensity dependent on a value detected;
- a liquid leakage decision unit configured to receive the signal output from the gas sensor at regular time intervals to determine whether liquid leakage of the solvent is present or not, the liquid leakage decision unit comprising,
  - a leak sensor value storage part configured to store a leak sensor value that is based on the intensity of the signal received from the gas sensor,
  - a difference calculation part configured to, when the signal is received from the gas sensor, identify the leak sensor value that is based on the intensity of the signal as a current leak sensor value, identify a leak sensor value that is based on an intensity of a signal previously received from the gas sensor as a previous leak sensor value, and calculate, as a difference value, a value obtained by subtracting the previous leak sensor value stored in the leak sensor value storage part from the current leak sensor value, and
  - a liquid leakage detection part configured to detect liquid leakage in the column oven by comparing the difference value calculated by the difference calculation part with a preset threshold,
- a calibration factor holding part configured to retain a calibration factor that represents a difference in sensitivity between different solvents in association with the gas sensor; and
- a sensor output calibration part configured to calibrate the signal received from the gas sensor by using the calibration factor retained in the calibration factor holding part, thereby to obtain the leak sensor value.

4. The column oven according to claim 3, wherein
the calibration factor holding part is configured to retain a second calibration factor determined so that the leak sensor value remains constant when a vaporized gas concentration of a particular solvent in the column oven is a predetermined concentration, and
the sensor output calibration part is configured to calibrate the signal received from the gas sensor using also the second calibration factor to obtain the leak sensor value.

5. The column oven according to claim 4, further comprising:
a temperature characteristic holding part configured to retain a temperature characteristic of the sensitivity of the gas sensor,
wherein
the sensor output calibration part is configured to calibrate the signal received from the gas sensor based also on the temperature characteristic retained in the temperature characteristic holding part to obtain the leak sensor value.

6. The column oven according to claim 5, further comprising:
a humidity characteristic holding part configured to retain a humidity characteristic of the sensitivity of the gas sensor,
wherein
the sensor output calibration part is configured to calibrate the signal received from the gas sensor based also on the humidity characteristic retained in the humidity characteristic holding part to obtain the leak sensor value.

7. The column oven according to claim 4, further comprising:
a humidity characteristic holding part configured to retain a humidity characteristic of the sensitivity of the gas sensor,
wherein
the sensor output calibration part is configured to calibrate the signal received from the gas sensor based also on the humidity characteristic retained in the humidity characteristic holding part to obtain the leak sensor value.

8. The column oven according to claim 3, further comprising:
a temperature characteristic holding part configured to retain a temperature characteristic of the sensitivity of the gas sensor,
wherein
the sensor output calibration part is configured to calibrate the signal received from the gas sensor based also on the temperature characteristic retained in the temperature characteristic holding part to obtain the leak sensor value.

9. The column oven according to claim 8, further comprising:
a humidity characteristic holding part configured to retain a humidity characteristic of the sensitivity of the gas sensor,
wherein
the sensor output calibration part is configured to calibrate the signal received from the gas sensor based also on the humidity characteristic retained in the humidity characteristic holding part to obtain the leak sensor value.

10. The column oven according to claim 3, further comprising:
a humidity characteristic holding part configured to retain a humidity characteristic of the sensitivity of the gas sensor,
wherein
the sensor output calibration part is configured to calibrate the signal received from the gas sensor based also on the humidity characteristic retained in the humidity characteristic holding part to obtain the leak sensor value.

11. A liquid chromatograph comprising:
a separation column;
a liquid feeder for feeding a mobile phase to an analysis channel having the separation column;
a sample injector for injecting a sample into the analysis channel between the liquid feeder and the separation column; and
a detector for detecting a sample component dissolved out of the separation column, wherein
the liquid chromatograph uses the column oven according to claim 3 as a column oven for adjusting a temperature of the separation column.

* * * * *